United States Patent
Borra et al.

(10) Patent No.: US 11,147,135 B2
(45) Date of Patent: Oct. 12, 2021

(54) LIGHTING SYSTEM THAT MAINTAINS MELANOPIC LUX LEVELS AT THE EYE REGARDLESS OF DISTANCE TO USER

(71) Applicant: SIGNIFY HOLDING B.V., Eindhoven (NL)

(72) Inventors: Tobias Borra, Eindhoven (NL); Lucas Josef Maria Schlangen, Eindhoven (NL); Jan Souman, Eindhoven (NL); Marcel Lucassen, Eindhoven (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 75 days.

(21) Appl. No.: 16/614,042

(22) PCT Filed: May 8, 2018

(86) PCT No.: PCT/EP2018/061887
§ 371 (c)(1),
(2) Date: Nov. 15, 2019

(87) PCT Pub. No.: WO2018/210636
PCT Pub. Date: Nov. 22, 2018

(65) Prior Publication Data
US 2021/0176841 A1    Jun. 10, 2021

(30) Foreign Application Priority Data
May 15, 2017  (EP) ..................................... 17171046

(51) Int. Cl.
*H05B 45/20* (2020.01)
*H05B 47/115* (2020.01)
(Continued)

(52) U.S. Cl.
CPC ............. *H05B 45/20* (2020.01); *H05B 45/10* (2020.01); *H05B 47/115* (2020.01); *H05B 47/17* (2020.01); *F21V 33/0052* (2013.01)

(58) Field of Classification Search
CPC .......... A61M 2021/0044; A61M 21/00; A61M 21/0094; A61M 21/02; A61M 2205/3306;
(Continued)

(56) References Cited

U.S. PATENT DOCUMENTS 10,599,116 B2 * 3/2020 Pillai .................. A61B 5/02055
10,600,213 B2 * 3/2020 Shih ...................... G06T 11/001
(Continued)

FOREIGN PATENT DOCUMENTS

CN         105612816 A      5/2016
DE    102013111662 A1      4/2015
(Continued)

OTHER PUBLICATIONS

L.L.A. Price, "Report on the First International Workshop on Circadian and Neurophysiological Photometry", 2013, pp. 1-39.
(Continued)

*Primary Examiner* — Monica C King (57) ABSTRACT

The invention provides a lighting system (1000) comprising:—a lighting device (100) configured to provide light (101);—a sensor (150) configured to sense a user-related parameter selected from one or more of (a) a distance parameter (d) between the lighting device (100) and a user (1) and (b) an eye-activity parameter of the eye (2) of the user (1); and—a control system (200) is configured to control one or more lighting properties selected from a spectral power distribution of the light (101) and a light intensity I of the light (101) as function of the user-related parameter.

18 Claims, 3 Drawing Sheets

(51) Int. Cl.
  *H05B 47/17* (2020.01)
  *H05B 45/10* (2020.01)
  *F21V 33/00* (2006.01)
(58) Field of Classification Search
  CPC .. A61M 2205/3368; A61M 2205/3569; A61M 2205/3592; A61M 2205/50; A61M 2205/584; H05B 45/10; H05B 45/20; H05B 45/24; H05B 45/37; H05B 47/105; H05B 33/08; H05B 45/22; H05B 45/28; H05B 45/3725; H05B 45/44; H05B 47/10; H05B 47/11; H05B 47/115; H05B 47/16; H05B 47/19
  See application file for complete search history.

(56) References Cited

U.S. PATENT DOCUMENTS

| | | | |
|---|---|---|---|
| 10,691,148 B2 * | 6/2020 | Pillai | G06F 3/165 |
| 2013/0099674 A1 | 4/2013 | Ferren | |
| 2014/0104436 A1 | 4/2014 | Bark | |
| 2015/0097490 A1 | 4/2015 | Okuya et al. | |
| 2015/0195885 A1 | 7/2015 | van de Ven et al. | |
| 2016/0073922 A1 | 3/2016 | Aguirre et al. | |
| 2016/0293140 A1 | 10/2016 | Li | |
| 2017/0086274 A1 | 3/2017 | Soler et al. | |
| 2017/0135176 A1 | 5/2017 | Soler et al. | |
| 2018/0043130 A1 * | 2/2018 | Moore-Ede | H05B 47/105 |

FOREIGN PATENT DOCUMENTS

| | | |
|---|---|---|
| WO | 2015156762 A1 | 10/2015 |
| WO | 2016008826 A2 | 1/2016 |
| WO | 2016049669 A1 | 4/2016 |
| WO | 2016145059 A1 | 9/2016 |

OTHER PUBLICATIONS

R.J. Lucas, et al., "Measuring and Using Light in the Melanopsin Age", Trends in Neurosciences, vol. 37, No. 1, Jan. 2014, pp. 1-9.

* cited by examiner

LIGHTING SYSTEM THAT MAINTAINS MELANOPIC LUX LEVELS AT THE EYE REGARDLESS OF DISTANCE TO USER

CROSS-REFERENCE TO PRIOR APPLICATIONS

This application is the U.S. National Phase application under 35 U.S.C. § 371 of International Application No. PCT/EP2018/061887, filed on May 8, 2018, which claims the benefit of European Patent Application No. 17171046.0, filed on May 15, 2017. These applications are hereby incorporated by reference herein.

FIELD OF THE INVENTION

The invention relates to a lighting system. The invention further relates to a method of controlling light, especially of such lighting system, and to a computer program product.

BACKGROUND OF THE INVENTION

Lighting systems with adjustable melatonin suppression effects are known in the art. US2015/0195885, for instance, describes a light emitting apparatus comprising a first LED component, a second LED component, and a control device, wherein the control device is arranged to operate the first LED component and the second LED component in a first operating mode in which combined emissions of the first LED component and the second LED component (i) are within six MacAdam ellipses of a target correlated color temperature, and (ii) embody a first melatonin suppression milliwatt per hundred lumens value, wherein the control device is arranged to operate the first LED component and the second LED component in a second operating mode in which combined emissions of the first LED component and the second LED component (i) are within six MacAdam ellipses of the target correlated color temperature, and (ii) embody a second melatonin suppression milliwatt per hundred lumens value that is at least about 10 percent greater than the first melatonin suppression milliwatt per hundred lumens value, and wherein the light emitting apparatus comprises at least one of the following features (a) to (c): (a) at least one of the first LED component and the second LED component comprises at least one LED arranged to stimulate emissions of at least one lumiphoric material, (b) combined emissions of the first LED component and the second LED component, when operated in the first operating mode, embody a color rendering index (CRI) value of at least about 80, (c) the light emitting apparatus comprises at least one element of a timer, a clock, a photo sensor, and at least one user input element, wherein the at least one element is arranged to trigger switching between the first operating mode and the second operating mode.

SUMMARY OF THE INVENTION

Critical to our sleep/wake cycle is melatonin, a hormone that promotes sleep during night time. Melatonin is a sleep supportive hormone that we only produce around (and during) our usual bedtime. Light exposure during the evening and at night suppresses the natural production of melatonin. When the spectrum of the light is shifted towards lower CCT and intensity levels (like during dawn and dusk), this reduces melatonin suppression and makes the light less disruptive for sleep. During day time, natural daylight with high correlated color temperature (CCT, herein also indicated as "color temperature") and intensity energizes people making them awake and alert. Current high performance LED based lighting apparatus with tunable CCT are able to mimic different phases of daylight, i.e., changes in spectral power distribution and variations in CCT, to a certain extent.

Figure 1:
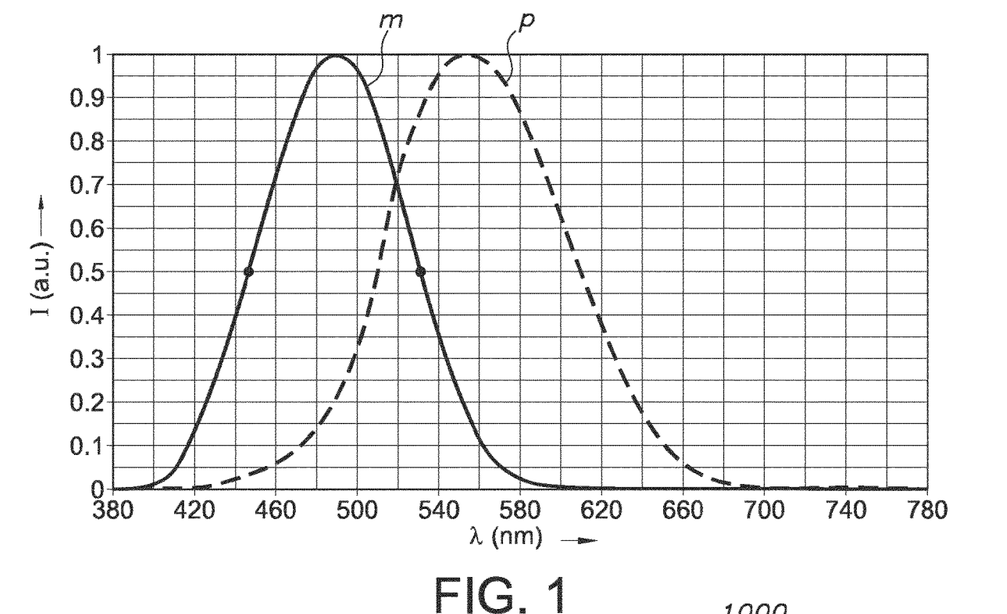
FIG. 1 shows the melanopic (solid line; curve m) and the photopic luminosity (dashed line; curve p) human eye normalized sensitivity functions (R. J. Lucas, et al., Measuring and using light in the melanopsin age, Trends in Neurosciences, Vol. 37, No. 1, January 2014, pp 1-9; http://www.sciencedirect.com/science/article/pii/S0166223613001975) (see also the report "CIE TN 003: 2015: Report on the First International Workshop on Circadian and Neurophysiological Photometry, 2013", with a link to an excel toolbox at http://cie.co.at/index.php?i_c-a_id=978 and http://files.cic.co.at/784_TN003_Toolbox.xls, respectively.

Next to the commonly known cones and rods, the human eye has melanopsin containing photoreceptors, affecting circadian entrainment and melatonin secretion, which are sensitive in a specific wavelength range. The relative spectral sensitivity for the classic receptors (rods and cones) and for the melanopic receptors are provided in FIG. 1 (see also R. J. Lucas, et al., Measuring and using light in the melanopsin age, Trends in Neurosciences, Vol. 37, No. 1, January 2014, pp. 1-9; http://www.sciencedirect.com/science/article/pii/S0166223613001975, the report "CIE TN 003:2015: Report on the First International Workshop on Circadian and Neurophysiological Photometry, 2013" at http://cie.co.at/index.php?i_ca_id=978 (with a link to an excel toolbox http://files.cie.co.at/784_TN003_Toolbox.xls). If the spectral power in the melanopic wavelength range is absent or low, the light exposure will be less suppressive for the melatonin hormone production thus enabling faster sleep onset and more consolidated sleep. If the spectral power in the melanopic range is increased, a nocturnal light exposure will result in stronger melatonin suppression. In general a light exposure can be said to be more biologically active and more alerting when the power in the melanopic range (and the ability to suppress melatonin at night) is increased. The effectiveness of a given light spectrum in suppressing melatonin production can be expressed in terms of the melanopsin effectiveness factor (MEF). This factor is calculated by multiplying the spectral power distribution of the light emitted by a lighting system (SPD($\lambda$)) with the melanopic sensitivity function (m($\lambda$)) divided by the product of SPD($\lambda$) and the photopic sensitivity (V($\lambda$)), normalized by the areas under the curves of m($\lambda$) and V($\lambda$), see equation 1 (and see also FIG. 1).

$$MEF = \left(\frac{\int_\lambda V(\lambda)d\lambda}{\int_\lambda m(\lambda)d\lambda}\right) \cdot \left(\frac{\int_\lambda SPD(\lambda)m(\lambda)d\lambda}{\int_\lambda SPD(\lambda)V(\lambda)d\lambda}\right) \quad \text{(eq. 1)}$$

This can be simplified to $$MEF = 1.22 \left(\frac{\int_\lambda SPD(\lambda)m(\lambda)d\lambda}{\int_\lambda SPD(\lambda)V(\lambda)d\lambda}\right) \quad \text{(eq. 2)}$$

as $$MEF = 1.22 \frac{\sum_{\lambda=380}^{780} SPD(\lambda)m(\lambda)\Delta\lambda}{\sum_{\lambda=380}^{780} SPD(\lambda)V(\lambda)\Delta\lambda} \quad \text{(eq. 3)}$$

Hence, the above indicated summations are over the visible range of 380-780 nm. By definition, the MEF for an equi-energy light source $MEF_{EE}$ equals 1. Especially, an equi-energy light source has SPD($\lambda$)=constant (for example 1) for all (visible) wavelengths.

For any kind of luminous radiation, the luminous flux ($\Phi_v$, expressed in lumen) is defined as:

$$\Phi_V = Km \int_\lambda SPD(\lambda)V(\lambda)d\lambda \quad \text{(eq. 4)}$$

$$\Phi_V = Km \sum_{\lambda=380}^{780} SPD(\lambda)V(\lambda)\Delta\lambda$$

wherein Km equals the maximum spectral luminous efficacy 683.002 lm/W and $V(\lambda)$ equals the photopic luminous efficiency function.

By combining eqs. 3 and 4, the melanopic flux or melanopic flux $\Phi_{mel}$, defined as $\Sigma(SPD(\lambda) \cdot m(\lambda) \cdot \Delta\lambda)$, can be calculated from the luminous flux according to $$\Phi_{mel} = \sum_{\lambda=380}^{780} SPD(\lambda)m(\lambda)\Delta\lambda = \quad \text{(eq. 5)}$$

$$\frac{MEF}{1.22}\sum_{\lambda=380}^{780} SPD(\lambda)V(\lambda)\Delta\lambda = \frac{MEF}{1.22}\frac{\Phi_V}{Km}$$

The melanopic illuminance ($E_{mel}$) is defined as the melanopic flux per unit area (A) and can be calculated according to $$E_{mel} = \Phi_{mel}/A = (MEF/1.22)*(E_v/Km) \quad \text{(eq. 6)}$$

where Ev represents the illuminance ($\Phi_v/A$) expressed in photopic lux.

Lucas et al. 2014 (Measuring and using light in the melanopsin age; Trends in Neurosciences, January 2014, vol. 37, no. 1, pages 1-9), introduced a new way to quantify light in terms of "(equivalent) melanopic illuminance" Ez, which is expressed in (equivalent) melanopic lux according to:

$$E_Z = Km \left( \frac{\sum_{\lambda=380}^{780} V(\lambda)\Delta\lambda}{\sum_{\lambda=380}^{780} \hat{m}(\lambda)\Delta\lambda} \right) \sum_{\lambda=380}^{780} SPD(\lambda)\hat{m}(\lambda)\Delta\lambda \quad \text{(eq. 7)}$$

$$= 72983.25 \sum_{\lambda=380}^{780} SPD(\lambda)\hat{m}(\lambda)\Delta\lambda$$

Here $\hat{m}(\lambda)$ represents the melanopic sensitivity function but now normalized according to $\Sigma_{\lambda=380}^{780}\hat{m}(\lambda)\Delta\lambda=1$ see also the manual (appendix 1) of the illuminance toolbox referred to in Lucas et al 2014.

By definition, an equi-energy light source that produces 1 (photopic) lumen on an area of 1 $m^2$ is said to produce a (equivalent) melanopic illuminance of one (1) "(equivalent) melanopic lux", and therefore also has a melanopic flux of one (1) "(equivalent) melanopic lumen".

According to this definition, the $E_z$ value (expressed in melanopic lux) of a test light condition t with a MEF value of $MEF_t$ and an illuminance of $E_v$ can be calculated from $E_{mel}$ (as defined in Eq. 6) according to $$E_z = \frac{\{E_{mel} \text{ of a test light condition} \atop t \text{ with } MEF_t \text{ and illuminance } Ev\}}{\{E_{mel} \text{ value of } equi \text{ energy} \atop \text{light with an illuminance of 1 lux}\}} = \quad \text{(eq. 8)}$$

$$\frac{(MEF_t/1.22)*(Ev/Km)}{(MEF_{EE}/1.22)*(1/Km)} = MEF_t * Ev$$

Similarly, the melanopic flux $\Phi_z$ (expressed in melanopic lumen) of a test light condition t with an MEF value of $MEF_t$ and a luminous flux of $\Phi_v$, can be calculated from $\Phi_{mel}$ (as defined in Eq. 5) according to $$\Phi_z = \frac{\{\Phi_{mel} \text{ of a test light condition} \atop t \text{ with } MEF_t \text{ and luminous flux } \Phi_V\}}{\{\Phi_{mel} \text{ value of } equi \text{ energy light} \atop \text{with an luminous flux of 1 lumen}\}} = \quad \text{(eq. 9)}$$

$$\frac{(MEF_t/1.22)*(\Phi_V/Km)}{(MEF_{EE}/1.22)*(1/Km)} = MEF_t * \Phi_V$$

As it may be desirable to take into account the circadian rhythm, it would be desirable to equip e.g. mobile devices (e.g. smartphones, tablets and laptops) with a solution that adapts the spectral light output of the screen to provide a predetermined melanopic lux level for the user. The reasoning here is that these solutions allow for a lower or higher melanopic flux at the eye position of the user, in order to either prevent undesired disruption of the circadian clock, or to strengthen the circadian clock.

However, such solution appears to hamper from the fact that not only intensity, such as evaluated by the melanopic flux, may be of relevance, but also the distance between user and source, such as the screen. In the technical field of lighting, the terms "intensity" and "flux/power" are often used interchangeably and relate to each other as intensity=flux/power per unit solid angle. The distance may have a substantial impact on the melanopic flux received at the eye position. In other words, a spectral distribution that changes with time in order to have a low impact on the circadian rhythm, like reducing the blue content received by a user during nocturnal times, may not have the desired effect when a user watches the display at a small distance (or at a smaller distance than an average distance to which the display may be optimized). Then, the blue content may still be (much) higher than desired.

Additionally, it seems that also another factor may influence the actual melanopic activation of the user, namely pupil size. A smaller pupil size may result in less light reaching the retina, whereas a larger pupil size may result in more light reaching the retina. A system that intends to control melanopic levels to which the user is really exposed may therefore especially need two types of information: the light output of the system and a distance to the user or light received by the eye of the user. Especially, in embodiments three types of information can be used: 1) the light output of the system; 2) the distance of the user to the system, and 3) the pupil size of the user. If one of these three information sources is not available or not taken into consideration, it may be difficult, if not impossible, to ascertain the actual melanopic levels to which the user is exposed. Since current systems do not take into account the abovementioned points 2) and 3), the melanopic activation of the user cannot be kept controlled (invalidating its intended use). A direct result hereof is that these current systems are fundamentally flawed.

Hence, it is an aspect of the invention to provide an alternative lighting system, which preferably further at least partly obviates one or more of above-described drawbacks. Yet, it is also an aspect of the invention to provide a method of controlling light which preferably further also at least partly obviates one or more of above-described drawbacks. Further, it is also an aspect of the invention to provide a method of controlling light which preferably further also at least partly obviates one or more of above-described drawbacks. The present invention may have as object to overcome or ameliorate at least one of the disadvantages of the prior art, or to provide a useful alternative.

Especially, in a first aspect the invention provides a light emitting system comprising: (i) a lighting device configured to provide light ("lighting device light"); (ii) a sensor configured to sense a user-related parameter selected from one or more of (a) a distance parameter ("d") between the lighting device and a user and (b) an eye-activity parameter of the eye of the user; and (iii) a control system is configured to control one or more lighting properties, especially selected from a spectral power distribution of the light and a light intensity ("I") of the light as function of the user-related parameter.

With such apparatus, it is possible to maintain a desired or necessary melanopic flux value for a user, irrespective of a distance or while changing a distance between the lighting device and the user. For instance, when moving a portable device with a display further away from the face of a user, the intensity may be increased. Likewise, when moving the display closer to the face, the intensity may be decreased. Alternatively or additionally, when moving the display closer to the face, the relative contribution in the blue, especially in the range of 450-490 nm, even more especially in the range of 460-490 nm, may be decreased. In this way, a (predetermined) melanopic flux may be substantially kept constant. For instance, it may be possible to maintain at night a constant low melanopic flux to prevent disruptive effects of the light on subsequent sleep. It may also allow a predefined lighting scheme, including a get to sleep period and a wake-up period, to be further modulated on the basis of the user-related parameter. Hence, it may be possible to keep a high melanopic flux value early in the morning, allowing for effective waking up, while slowly increasing light intensity and/or color temperature to ensure maximal visual comfort just after waking up and at the same time minimizing disruptions of such high melanopic flux scheme due to a decrease or increase in distance between the user and the lighting device or display, which variable distance may in principle—without the herein proposed solution—reverse the scheme. The invention also allows maintaining the melanopic flux value at a desired or preset level (herein also indicated as "predetermined level"), while tuning one or more other lighting properties, e.g. in conformance with personal preferences or in conformance with lighting of surrounding spaces.

Hence, as also indicated above such apparatus may be used for maintaining the melanopic illuminance constant within a predetermined range (of the melanopic lux). Therefore, the control system may in embodiments be configured to control one or more lighting properties, especially selected from a spectral power distribution of the light and a light intensity (I) of the light as function of the user-related parameter for maintaining the melanopic lux level constant within a predetermined range. Herein, the term "within a predetermined range" indicates that the value may be constant, but may also be constant within a range of e.g. +/−20% from a predetermined value. Hence, the term "constant" may especially refer to substantially constant. The term "substantially constant" may e.g. imply changes within +/−20%, such as within +/−10%, like within +/−5%, of a predetermined value. Further, it may (also) be possible that over a part of the distance parameter the melanopic lux is constant.

As indicated above, the invention provides a light emitting system. The light emitting system may e.g. comprise a backlighting device in a display or a mobile device. The light emitting system may comprise an indoor lighting device at home, in a workplace, in a hotel room, in a healthcare setting, in an office. The light emitting system may comprise light therapy devices, etcetera. The lighting system may be office lighting, etc.

In specific embodiments, the lighting system comprises a portable device. Portable devices may include mobile computers (such as mobile internet devices, tablet computers ("tablets"), wearable computers ("wearables", such as calculator watches, smartwatches, head-mounted displays), personal digital assistants, enterprise digital assistants, calculators, handheld game consoles, portable media players, ultra-mobile pcs, digital media players, digital still cameras (DSC), digital video cameras (DVC) or digital camcorders, mobile phones (such as smartphones, feature phones, iPhones) (also indicated as "cell phones"), pagers, personal navigation devices (PND), smart cards, project ara, etcetera.

Hence, especially the light emitting system comprises a portable device, wherein the portable device comprises a display comprising the lighting device, wherein the portable device further comprises the sensor and the control system. Even more especially, the portable device is selected from the group consisting of a smartphone, a laptop, a tablet, a wearable device, a personal digital assistant, a game console, a media player, and a navigation device. The invention may especially be of relevance for portable devices, as these are generally dedicated for a single user and the single user in general defines the distance to the mobile device.

Hence, in embodiments the main function of the "light emitting system" may not be to provide light, such as in the case of a luminaire, but to provide information using a display. A display provides light, and thereby, a display based light emitting system emits light. Note that the light emitting system, especially the display, is configured to provide white light that is composed of different colors of light, or colored light, wherein the color of the light is tunable.

The term white light herein, is known to the person skilled in the art. It especially relates to light having a correlated color temperature (CCT) between about 1,500 and 20,000 K, especially 2,000-20,000 K, for general lighting especially in the range of about 2,000 K and 6,500 K, and for backlighting purposes especially in the range of about 7,000 K and 20,000 K, and especially within about 15 SDCM (standard deviation of color matching) from the BBL (black body locus), especially within about 10 SDCM from the BBL, even more especially within about 5 SDCM from the BBL. Especially thus, the light emitting system comprises a plurality of light sources. Even more especially, the light emitting system comprises a plurality of different light sources which are configured to provide light source light in different parts of the visible spectrum, and wherein the different light sources are individually controllable.

Hence, in embodiments the light emitting system may comprise or may be a backlighting device. Alternatively, in embodiments the light emitting system may comprise or may be an direct light emitting device such as an LED array or OLED device.

In other embodiments, the light emitting system may be configured to provide colored light.

In yet further embodiments, the light emitting system may be configured to provide in a mode of operation colored light. The term "mode" may also be indicated as "controlling mode" (see further also below).

Further, the term "lighting device" may refer to one or more lighting devices. The term "light source" may also relate to a plurality of light sources, such e.g. as 2-200 (solid state) LED light sources. Hence, the term LED may also refer to a plurality of LEDs. Further, the terms "light source" or "lighting device" may in embodiments also refer to a so-called chips-on-board (COB) light source. The term "COB" especially refers to LED chips in the form of a semiconductor chip that is neither encased nor connected but directly mounted onto a substrate, such as a PCB. Hence, a plurality of semiconductor light sources may be configured on the same substrate. In embodiments, a COB is a multi LED chip configured together as a single lighting module. In embodiments, the light emitting system comprises one or more laser light sources. Hence, the term "light source" may in embodiments refer to one or more (different) laser light sources.

The light generated during use of the apparatus is indicated as light or lighting device light. The lighting device is adapted to provide lighting device light that has tunable lighting properties. Lighting properties that are tunable may especially be selected from the group consisting of spectral power distribution of the light, correlated color temperature (CCT), color point, relative gamut area index, and intensity of the light. Therefore, the light emitting system comprises a lighting device configured to provide (during operation of the lighting device) lighting device light having tunable lighting properties.

Further, the lighting system comprises a sensor configured to sense a user-related parameter. The user-related parameter is especially related to the amount of light that the eye(s) of the user receive. Hence, a user-related parameter may include the distance between the display and the eye(s). The user-related parameter may also include e.g. the pupil size. Hence, in embodiments the user-related parameter may be selected from one or more of (a) a distance parameter d between the lighting device and a user and (b) an eye-activity parameter of the eye of the user.

The distance between the lighting device, especially the display, and the user, may be most relevant. In embodiments, a sensor may be used that senses the distance between the sensor and the user. Hence, depending on the location of the sensor, there may be a (very) slight difference between the distances between the lighting device and the user and between the sensor and the user. For example, the sensor may be incorporated in the lighting device and measure a distance from the device towards the face of the user or the sensor may be incorporated in smart glasses worn by the user and measure a distance from the glasses towards the device. Further, as an estimate of the distance, also infrared radiation (IR) may be used, as more thermal energy may be received/sensed when the head of the user is closer to the sensor than when the head of the user is further away. In embodiments, a sensor may be used that is configured to sense reflected light (such as light reflected from the user). Therefore, in embodiments the sensor may be configured to sense one or more of infrared radiation, and reflected light.

One or more (different types) of sensors may be applied for sensing the distance parameter.

Hence, herein the term "distance parameter" is used, which reflects the distance (or proximity) of the user, especially the eye(s) of the user, from the lighting device, such as a display.

The eye-activity parameter reflects how much light is received by the user. For instance, large pupils may indicate a low illuminance at the eyes and small pupils may indicate a relatively high illuminance at the eyes. The melanopic effect relates to the amount of melanopsin active light received at the retina of the user's eyes (received photons), which is determined by the melanopic illuminance at the eyes (available photons) and the pupil size (diaphragm). Hence, in embodiments the eye-activity parameter comprises a pupil size. Alternatively or additionally, the eye-lid closure may be used as measure. Therefore, in embodiments the eye-activity parameter comprises an eyelid closure (i.e. especially the extent of eyelid closure or the eyelid closure size). Further, changes in pupil size and/or eyelid closure may also be relevant. Hence, in embodiments the eye-activity parameter comprises a pupil size change and/or an eyelid closure change. Therefore, in embodiments the eye-activity parameter comprises one or more of a pupil size, a pupil size change, an eyelid closure, and a change in an eyelid closure.

Eyelid closure or eyelid (closure) dynamics may be used as an indicator of fatigue or drowsiness. High MEF light may be used to keep people more awake. Therefore, the present invention may in embodiments e.g. include providing high MEF light, for instance for combatting user fatigue.

In embodiments the sensor may be configured to sense an eye-activity parameter of the eye of the user. In embodiments, the sensor may comprise a camera, such as a CCD camera. Such camera may be available by handheld devices (at the display side of such device) anyhow. Alternatively, such camera may be available as an inward facing camera in smart glasses worn by the user and adapted to measure an eye-activity parameter of the eye of the user.

Therefore, according to embodiments of the invention, the melanopic illuminance at the user's eyes may be maintained with a predetermined range of melanopic lux values, based on an eye-activity parameter, to compensate for variations of, for example, pupil size or degree of eyelid closure which change the effectively received melanopic illuminance at the retina of the user's eyes.

Further, the light emitting system comprises a control system configured to control one or more lighting properties selected from (i) a spectral power distribution of the light, and (ii) the light intensity of the light as function of the user-related parameter.

The term "controlling" and similar terms especially refer at least to determining the behavior or supervising the running of an element. Hence, herein "controlling" and similar terms may e.g. refer to imposing behavior to the element (determining the behavior or supervising the running of an element), etc., such as e.g. measuring, displaying, actuating, opening, shifting, changing temperature, etc. Beyond that, the term "controlling" and similar terms may additionally include monitoring. Hence, the term "controlling" and similar terms may include imposing behavior on an element and also imposing behavior on an element and monitoring the element.

The term "controllable" in the context of lighting properties especially refers to the possibility that a plurality of values, especially more than two, can be chosen for a respective lighting property. Hence, referring to intensity, "controllable" may imply a plurality of different intensity values between zero and maximum intensity. Referring to color point, "controllable" may imply the possibility of selecting a plurality of different x-values and y-values (referring to the CIE 1931 color space). Hence, one or more lighting properties, also including the spectral power distribution, of the light are controllable.

The control system may also control one or more lighting properties based on the input of a (day)light sensor or may control one or more lighting properties based on a predefined (time) scheme. In the latter case, the control system may substantially autonomously select the predetermined melanopic flux value based on the predefined (time) schema. The control system may control the light based on the input of a (day)light sensor and adapt the light provided by the lighting system while taking into account (as much as possible) the already available (day) light. Further, the control system may be configured to control the light as function of an activity of a user. The type (and optionally intensity of the) activity may be retrieved from a device, a sensor, or a user input.

Here, the terms "maintaining" or "substantially the same" or "constant", may especially refer to a change in value (of the melanopic flux value) of equal to or less than 20%, such as equal to or less than 10%. Hence, the word "maintaining" and similar terms may also refer to "substantially maintaining", or maintaining with some tolerance, which, as indicated above, may e.g. be in the range of about +/−20%, such as about +/−10%, like especially about +/−5%.

As is known in the art, the intensity in terms of illuminance of the light of a single light source received at a surface scales with the square distance. Hence, when the distance decreases, the intensity received by the eye increases. In embodiments, the control system may be configured to dim the light. This dimming may follow the square law, though a smaller dependence of intensity from distance may also be desired, for instance to have smaller light intensity variations when distance changes. Although this may result in the illuminance not being maintained exactly the same, the illuminance may still be maintained within a predetermined range. The predetermined range then allows for deviations from the inverse-square law.

Therefore, in specific embodiments the control system is configured to maintain in a mode a value of $I/(\alpha d^n)$ constant over at least part of a range of the distance parameter d, wherein I is the luminous intensity of the light of the lighting device, and wherein $0 < \alpha \leq 1$ and $1 \leq n \leq 2$. The parameter $\alpha$ may be used to influence the relation between distance parameter and intensity. Also the parameter n may be used to influence the relation between distance parameter and intensity. With $\alpha$ being 1 and n being 2, the square law is followed. Here, in this formula, the intensity I may in embodiments especially refer to the intensity of the light provided. In this way, the illuminance at the eye may be kept within a predetermined range.

Alternatively or additionally, the control system may also be configured to change the spectral distribution of the light as function of the distance parameter. For instance, the color temperature may decrease with decreasing distance. This leads to a reduction in blue content of the emitted light which may e.g. be helpful, especially in nocturnal situations, not to disturb the circadian rhythm. Also in this way, the illuminance at the eye may be kept at a predetermined level (if desired).

As indicated above, the system may include a mode of operation. The term "mode" may also be indicated as "controlling mode" (see also above). This does not exclude that the system may also be adapted for providing another controlling mode, or a plurality of other controlling modes. However, the control system is adapted to provide at least a controlling mode. Would other modes be available, the choice of such modes may especially be executed via a user interface, though other options, like executing a mode in dependence of a sensor signal or a (time) scheme may also be possible.

As the light emitting system may be able to change the spectral distribution and the intensity, it may also be possible to control the melanopic flux of the light.

Therefore, in embodiments the light emitting system is configured to control in a mode the melanopic flux of the light as a function of the user-related parameter. In specific embodiments, the light emitting system is configured to maintain a value of $\Phi_{mel}/(\alpha d^n)$ constant (i.e. at a predetermined level) over at least part of a range of the distance parameter d, wherein $\Phi_{mel}$ is the melanopic flux of the light of the lighting device, and wherein $0 < \alpha \leq 1$ and $1 \leq n \leq 2$.

Hence, in embodiments the control system is configured to scale the light intensity I of the light with the distance parameter d in one or more of a linear way and an exponential way. The phrase "in one or more of a linear way and an exponential way" may refer to the fact that the scaling may have a linear and an exponential character. Further, the phrase "in one or more of a linear way and an exponential way" may also indicate that over e.g. part of the distance parameter range the scaling is exponential and over another part the scaling may be linear. In a full linear scaling, n, as defined above, may be 1. In a full exponential scaling, n, as defined above, may be 2.

Dependent upon the lighting property chosen, changing such property may lead to a visible change in the emitted light, whereas changing the melanopic flux can be done while keeping e.g. the color point constant. Likewise, the melanopic flux can be constant while changing the color point or color temperature of the emitted light, etc.

As indicated above, a parameter may be kept constant over at least part of a range of the distance parameter. Especially, assuming a portable device a distance parameter range may be associated with such device. For instance, for a laptop the distance parameter may relate to a distance of about 30-60 cm. For a cell phone, the distance parameter may relate to a distance of about 20-50 cm. In specific embodiments, the maximum of the distance parameter may relate to about an arm length, such as about 30-90 cm (also taking into account juvenile users).

A full compliance with the square distance law over such lengths may lead to relatively large intensity changes. Likewise, when desiring to maintain a predetermined melanopic illuminance or flux density received by the human eye this may lead to substantial spectral changes and/or may only be possible over a part of the range of the distance parameter.

Hence, in more general embodiments, a first intensity value $I_1$ may be defined as the product of the luminous power $\Phi$ (of the lighting device) and the inverse distance parameter (1/d), $I_1=P/d$, wherein the control system is configured in a mode to keep the first intensity value constant or to decrease the first intensity value with decreasing distance parameter over at least part of the range of the distance parameter, and/or (optionally) to keep the first intensity value constant or to increase the first intensity value with increasing distance parameter over at least part of the range of the distance parameter.

In yet further more general embodiments, a second intensity value $I_2$ may be defined as the product of the luminous power $\Phi_2$ (of the lighting device) in the spectral range of 450-490 nm and the inverse distance parameter (1/d), $I_2=P_2/d$, wherein the control system is configured in a mode to keep the second intensity value constant or to decrease the second intensity value with decreasing distance parameter over at least part of the range of the distance parameter, and/or (optionally) to keep the second intensity value constant or to increase the second intensity value with increasing distance parameter over at least part of the range of the distance parameter.

In yet further more general embodiments, a third intensity value $I_3$ may be defined as the product of the melanopic power, also referred to herein as melanopic power ($\Phi_{mel}$), and the inverse distance parameter (1/d), $I_3=\Phi_{mel}/d$, wherein the control system is configured in a mode to keep the third intensity value constant or to decrease the third intensity value with decreasing distance parameter over at least part of the range of the distance parameter, and/or (optionally) to keep the third intensity value constant or to increase the third intensity value with increasing distance parameter over at least part of the range of the distance parameter. As indicated above, in embodiments $\Phi_{mel}/(d^2)$ may be constant.

When the melanopic flux divided by the square distance stays constant, then in fact the melanopic illuminance stays constant. This may be desirable. For instance, during daytime the melanopic illuminance at the eye of the user may exceed 400 melanopic lux (to secure sufficient subjective alertness, moreover, a high daytime melanopic flux also strengthens the body clock and the circadian rhythm), while at night it may be below 40 melanopic lux (to prevent sleep disruption). Hence, the desired melanopic flux need not be constant but can also vary over time.

Therefore, in embodiments the control system is configured to maintain a predetermined melanopic illuminance ($E_{mel}$). Especially, in further embodiments the light emitting system may further comprise a user interface configured to allow a user to determine the predetermined melanopic illuminance ($E_{mel}$).

Hence, it may thus also be desirable not to exceed a certain melanopic illuminance (which maximum value may e.g. be lower during nocturnal times than during daytime), or to drop below a certain melanopic illuminance (especially during the day time). Therefore, in further embodiments the control system may be configured to control the melanopic illuminance ($E_{mel}$) to be not larger than a (first) predetermined maximum melanopic illuminance value and/or to be not smaller than a (second) predetermined minimum melanopic illuminance value.

As indicated above, one may e.g. define a minimum value of a lighting property or a combination of minimum values for lighting properties and/or one may e.g. define a maximum value of a lighting property or a combination of maximum values for lighting properties. However, it may also be possible to have lighting property values defined with a time dependency, such as function of the time of the day. Still, the control system may control the lighting properties as function of a user-related parameter, but will also take into account the—at that moment in time—programmed value(s) or range(s) of melanopic illuminance.

Hence, in embodiments the control system is configured to control the light according to a predefined scheme, and wherein the control system is further configured to adapt the light relative to the predefined scheme and as function of the user-related parameter (such as the distance parameter).

As indicated above, the term "predetermined melanopic flux value" does not necessarily mean that the melanopic flux value is eternally fixed. The melanopic flux value may also vary according to a (predetermined) time scheme or in dependence of a (predetermined) sensor signal value, such as from a (day)light sensor. However, the control system determines the melanopic flux value in dependence of such a sensor signal value or according a time in such time scheme and as long as the control system does not change the so determined melanopic flux value, the so determined melanopic flux value is the predetermined melanopic flux value from which, in the herein indicated mode, substantially no deviation is allowed. Would for instance the control system change the melanopic flux value, e.g. because of a changed (day)light intensity level or due to a changed time value, then the changed melanopic flux value is the predetermined melanopic flux value, from which, in the herein indicated mode, substantially no deviation is allowed.

Therefore, in embodiments the control system may be adapted to provide at least a controlling mode which comprises controlling the melanopic flux of the light in dependence of a ((day)light) sensor signal, wherein a temporary predetermined melanopic flux value is defined by said control system, and wherein said controlling mode comprises maintaining said temporary predetermined melanopic flux value while allowing another lighting property of the light to be changed from a first lighting property value to a second lighting property value. The control system may define the temporary predetermined melanopic flux value based on a predefined scheme comprising one or more relations between sensor signals and melanopic flux values. Other sensor signal(s) than a (day)light sensor signal may also be used as input, either additionally or alternatively, such as a presence sensor, a temperature sensor, etc.

Therefore, in yet other embodiments, which may be combined with the former embodiments related to the ((day)light) sensor, the control system may (also) be adapted to provide at least a controlling mode which comprises controlling the melanopic flux of the light as function of a time scheme defining the melanopic flux of the light as function of one or more of time, day, week, month, and season, wherein a temporary predetermined melanopic flux value is defined by said control system, and wherein said controlling mode comprises maintaining said temporary predetermined melanopic flux value while allowing another lighting property of the light to be changed from a first lighting property value to a second lighting property value. In embodiments, the time scheme may include a calendar. In embodiments, the time scheme may include information about activities and/or activity periods and/or rest periods. In further embodiments, the time scheme may be based on circadian rhythm data, etc.

Especially, at least the spectral power distribution of the light is controllable as well as another lighting property selected from the group consisting of correlated color temperature, color point, and intensity of the light. Note that different spectral power distributions may provide the same color point or correlated color temperature.

Further, in general also the intensity of the light will be controllable. Further, in general also the color point and/or correlated color temperature of the light will be controllable.

Hence, in general the lighting device will comprise a plurality of light sources configured to provide light source light having different spectral power distributions.

In yet other embodiments, it may also be possible to influence the predetermined melanopic flux value determined by the control system. For instance, the control system may allow input such as "low", "medium", "high", etc. from a user interface. Hence, the control system may include a user interface device, such as a graphical user interface device and/or may functionally be coupled to a user interface device such as a computer, smart phone, I-phone, etc. The melanopic flux value itself may also be selected by a user, e.g. via such user interface. The selected melanopic flux value may then be defined as the predetermined melanopic flux value. The user may in embodiments also be able to select a value, status, etc. that reflects a certain melanopic flux or that reflects a certain melanopic flux at certain conditions such as early in the morning or under specific lighting conditions. For instance, it may also be possible that the user may select options like "sleep", "wake up", "high alert", "reading", "working", etc. This may then be translated by the control system into a predetermined melanopic flux. Hence, the user may select input values and/or conditions and the control system may include a routine which define the predetermined melanopic flux based thereon. For instance, the predetermined melanopic flux may be dependent upon the time of the day, day of the week, etc. Instead of the term "routine" also the term "scheme" or "program" may be used.

As will be clear from the above, the predetermined melanopic flux value may in embodiments be a fixed value, but may in other embodiments be a variable (temporary fixed) value, e.g. variable based on a ((day)light) sensor, a time scheme, user interface input, etc.

The one or more other lighting properties, other than the melanopic flux, may also be controlled with the control system. Hence, the control system may control based on the input of a sensor, such as a (day)light sensor, or may control based on a predefined (time) scheme, etc., one or more of the other lighting properties. Alternatively or additionally, one or more other lighting properties may be selected by a user via a user interface. Hence, controlling a lighting property may include controlling such lighting property in dependence of one or more of a sensor signal, a (time) scheme, and a user input value or instruction.

When changing the spectral power distribution, such as e.g. to maintain or set a specific melanopic flux, other lighting properties like color point, color temperature, etc. may also change. It may however be desirable to change the spectral power distribution such that the desired melanopic flux is obtained without changing other lighting properties, or only changing these with relatively small amounts. It may also be desirable to change the melanopic flux with a change in the user-related parameter, such that one or more of the illuminance, the illuminance in the 440-490 nm region and the melanopic illuminance value stay substantially constant, while optionally maintain other lighting properties constant. Therefore, in embodiments the control system is configured to control the spectral power distribution of the light as function of the user-related parameter, while maintaining one or more other lighting properties constant, wherein the one or more other light properties are especially selected from the group consisting of the correlated color temperature and the color point.

As a manual change of the distance between the user and a mobile device may be relatively abrupt but may also be easily (partially) undone, or may include minor changes due to normal (or health condition caused) variations in time such as normal variations in the range of up to about 2 cm, it may be desirable to include some delay or smoothing of the changes in the lighting device light. Therefore, in embodiments the control system may be configured to adapt the one or more lighting properties selected from (i) a spectral power distribution of the light, and (ii) the light intensity I of the light as function of a change in the user-related parameter, wherein the adaptation is only executed after a predetermined period of substained change in the user-related parameter. Hence, when during a predetermined time (after a change) the change has not substantially altered, the control system may adapt the one or more lighting properties.

Alternatively or additionally, the control system may be configured to adapt the one or more lighting properties selected from (i) a spectral power distribution of the light, and (ii) the light intensity I of the light as function of an average change, within a predetermined time period, in the user-related parameter. Further, alternatively or additionally, the control system may be configured to gradually adapt the one or more lighting properties as function of a change in the user-related parameter.

As will be clear to a person skilled in the art, in embodiments the control system may be configured to permanently or regularly update the user-related parameter and consequently adapt the one or more lighting properties.

It appears to be useful to have two sources of blue light, which sources have a different overlap with the melanopic sensitivity curve. In such a way, blue light may be provided for generating white light while being able to vary the melanopic flux of the white light. Therefore, in specific embodiments the lighting device comprises a source of deep blue light, a source of blue light, a source of green light, and a source of red light, which are independently controllable by the control system, wherein the source of deep blue light is configured to generate light selected from the wavelength range of 400-440 nm and having a peak wavelength at a smaller wavelength then a peak wavelength of the light of the source of blue light. The source of blue light may especially be configured to generate light selected from the range of 440-490. The phrase "light selected from the wavelength range of 400-440 nm" and similar phrase especially indicate that the peak wavelength of the light may be found in such spectral range. Hence, a source of light having a peak wavelength in the range of 400-400 nm, and a source of light having a peak wavelength in the range of 440-490 nm may be available.

Hence, the lighting device or lighting system may be part of or may be applied in e.g. office lighting systems, household application systems, shop lighting systems, home lighting systems, accent lighting systems, spot lighting systems, theater lighting systems, fiber-optics application systems, projection systems, self-lit display systems, pixelated display systems, segmented display systems, warning sign systems, medical lighting application systems, indicator sign systems, decorative lighting systems, portable systems, automotive applications, (outdoor) road lighting systems, urban lighting systems, green house lighting systems, horticulture lighting, or LCD backlighting.

As indicated above, the lighting device or lighting system may be used as backlighting unit in an LCD display device. Hence, the invention provides also a LCD display device comprising the lighting unit as defined herein, configured as a backlighting unit. The invention also provides in a further aspect a liquid crystal display device comprising a backlighting unit, wherein the backlighting unit comprises one or more lighting devices as defined herein. Therefore, an aspect the invention also provides an electronic device comprising a backlighting unit, wherein the electronic device comprises the lighting system as defined herein and said backlighting unit comprises said lighting device. Such electronic device may also include a plurality of lighting systems and/or a plurality of lighting devices. In further embodiments, the electronic device comprises the lighting system as defined herein, wherein said backlighting unit comprises a plurality of the lighting devices. The electronic device may e.g. be selected from the group consisting of a display and a mobile device such as a smart phone, an iPhone, a tablet, etc. etc.

In yet a further aspect, the invention also provides a method of controlling light, wherein one or more lighting properties, including the spectral power distribution and the intensity I of the light are controllable, the method comprising (i) providing said light; (ii) sensing a user-related parameter selected from one or more of a distance parameter d between the lighting device and a user and an eye-activity parameter of the eye of the user; and (iii) controlling one or more lighting properties selected from a spectral power distribution of the light and a light intensity I of the light as function of the user-related parameter. The method may e.g. be executed with the herein described system. Such method may in embodiments especially be used for maintaining the melanopic flux constant within a predetermined range of the melanopic flux.

Yet in a further aspect, the invention also provides a computer program product, when running on a computer which is functionally coupled to a lighting device, is capable of bringing about the method as described herein, wherein the lighting device is configured to provide light, wherein one or more lighting properties, including the spectral power distribution and the intensity of the light, are controllable.

In yet a further aspect, the invention also provides a data carrier having stored thereon program instructions, which when executed by a processing apparatus, causes the processing apparatus, optionally by operating together with one or more other processing apparatus, to execute the method as defined herein. Instead of the term "data carrier" also the terms "record carrier" etc. may be used. The record carrier, such as a USB stick, a CD, a DVD, etc. may store a computer program for executing the herein described method when run on one or more other processing apparatus. Hence, the computer program product, when running on a computer or loaded into a computer, brings about, or is capable of bringing about, the method as described herein. The computer-readable medium and/or memory may be any recordable medium (e.g., RAM, ROM, removable memory, CD-ROM, hard drives, DVD, floppy disks or memory cards) or may be a transmission medium (e.g., a network comprising fiber-optics, the world-wide web, cables, and/or a wireless channel using, for example, time-division multiple access, code-division multiple access, or other wireless communication systems). Any medium known or developed that can store information suitable for use with a computer system may be used as the computer-readable medium and/or memory.

BRIEF DESCRIPTION OF THE DRAWINGS

Embodiments of the invention will now be described, by way of example only, with reference to the accompanying schematic drawings in which corresponding reference symbols indicate corresponding parts, and in which.

The schematic drawings are not necessarily on scale.

DETAILED DESCRIPTION OF THE EMBODIMENTS

FIG. 1 shows the relative melanopic (m) and photopic (p) human eye sensitivity functions. The maximum sensitivity for the melanopic function is at 490 nm, the full width half maximum values are at 447 nm and 531 nm.

| lambda (nm) | sensitivity |
| --- | --- |
| 380 | 9.18E−04 |
| 385 | 1.67E−03 |
| 390 | 3.09E−03 |
| 395 | 5.88E−03 |
| 400 | 1.14E−02 |
| 405 | 2.28E−02 |
| 410 | 4.62E−02 |
| 415 | 7.95E−02 |
| 420 | 1.37E−01 |
| 425 | 1.87E−01 |
| 430 | 2.54E−01 |
| 435 | 3.21E−01 |
| 440 | 4.02E−01 |
| 445 | 4.74E−01 |
| 450 | 5.54E−01 |
| 455 | 6.30E−01 |
| 460 | 7.08E−01 |
| 465 | 7.85E−01 |
| 470 | 8.60E−01 |
| 475 | 9.18E−01 |
| 480 | 9.66E−01 |
| 485 | 9.91E−01 |
| 490 | 1.00E+00 |
| 495 | 9.92E−01 |
| 500 | 9.66E−01 |
| 505 | 9.22E−01 |
| 510 | 8.63E−01 |
| 515 | 7.85E−01 |
| 520 | 7.00E−01 |
| 525 | 6.09E−01 |
| 530 | 5.19E−01 |
| 535 | 4.33E−01 |
| 540 | 3.52E−01 |
| 545 | 2.79E−01 |
| 550 | 2.16E−01 |
| 555 | 1.62E−01 |
| 560 | 1.19E−01 |
| 565 | 8.43E−02 |
| 570 | 5.87E−02 |
| 575 | 4.00E−02 |
| 580 | 2.69E−02 |
| 585 | 1.79E−02 |
| 590 | 1.18E−02 |
| 595 | 7.73E−03 |
| 600 | 5.07E−03 |
| 605 | 3.32E−03 |
| 610 | 2.18E−03 |
| 615 | 1.43E−03 |
| 620 | 9.47E−04 |
| 625 | 6.28E−04 |
| 630 | 4.18E−04 |
| 635 | 2.80E−04 |
| 640 | 1.88E−04 |
| 645 | 1.27E−04 |
| 650 | 8.66E−05 |
| 655 | 5.92E−05 |
| 660 | 4.07E−05 |
| 665 | 2.81E−05 |

| lambda (nm) | sensitivity |
| --- | --- |
| 670 | 1.96E−05 |
| 675 | 1.36E−05 |
| 680 | 9.58E−06 |
| 685 | 6.75E−06 |
| 690 | 4.79E−06 |
| 695 | 3.41E−06 |
| 700 | 2.44E−06 |
| 705 | 1.75E−06 |
| 710 | 1.27E−06 |
| 715 | 9.18E−07 |
| 720 | 6.69E−07 |
| 725 | 4.9E−07 |
| 730 | 3.6E−07 |
| 735 | 2.65E−07 |
| 740 | 1.97E−07 |
| 745 | 1.46E−07 |
| 750 | 1.09E−07 |
| 755 | 8.2E−08 |
| 760 | 6.17E−08 |
| 765 | 4.66E−08 |
| 770 | 3.53E−08 |
| 775 | 2.69E−08 |
| 780 | 2.05E−08 |

Amongst others herein a lighting system (or light emitting system) is proposed that comprises at least one light source (or lighting device), and at least one (programmed) controller and at least one sensor, where the sensor for instance detects the distance of the (eye of the) user to the lighting system, e.g. by a proximity sensor or a camera, and/or detects pupil size of the user, e.g. by image segmentation of a camera image or using a separate sensor, and wherein the controller is for instance configured to vary at least one light property of the light output of the system, in such a way that, at least during part of the time, the amount of melanopic activation at the eye of the user (melanopic illuminance or melanopic flux) as generated by the system is kept virtually constant to a predetermined setting of the system or as indicated by the user, as a function of distance to the lighting system and pupil size (or changes for instance less than 10%).

In an execution of the various embodiments the controller varies an intensity of the light and initiates a smooth change such as a ramp up or ramp down in the light intensity to prevent sudden changes in light output from the lighting system. In another execution, the user him/herself indicates the distance to the light device, whereby the system generates the spectral composition to reach the target melanopic lux levels at the eye position of the user based on the indicated distance. In yet another execution, pupil size is directly extracted from sensor data (e.g. by image segmentation) or estimated, in case this data is unreliable or not available, from the actual light output of the system and the distance of the user to the light system.

In an embodiment, the system may adjust the photopic light output of the light system in such a way that the melanopic lux level at the eye is kept close to a target setting (target setting may be either directly given by the user, or is a predetermined setting by the system). This may be for instance a high melanopic lux setting for the morning, or a low melanopic lux setting for the evening. The melanopic effect experienced by the user is then substantially maintained by taking the distance of the user to the lighting device and the pupil size of the user into account and adjusting the total light output (luminous flux) of the lighting device to keep melanopic lux value at the eye position within a predetermined range. This will result in a lighting system that will effectively turn brighter or darker as a function of user distance and pupil size in order to keep melanopic values experienced by the user constant, or with less than 10% change.

In an embodiment, the system may adjust the correlated color temperature (CCT) of the lighting system in such a way that the melanopic lux at the eye is kept close to a target setting (target setting may be either directly given by the user, or is a predetermined setting by the system). The melanopic effect experienced by the user is then kept constant by taking the distance of the user to the lighting system and the pupil size of the user into account and adjusting the spectral composition (spectral power distribution) of the light output. This will result in a lighting system where correlated color temperature (CCT) will decrease when distance between the lighting system and the user decreases, and increase when the distance between the lighting system and the user increases, while illuminance or total photopic lux level at the eye position remains constant.

In an embodiment, the system may adjust both photopic luminous flux and CCT in such a way that the melanopic illuminance at the eye is kept close to a target setting when the distance between user and light source changes.

In an embodiment, the system may adjust the melanopic output of the lighting device to a target setting (target setting may be either directly given by the user or provided as a predetermined setting by the system). The melanopic effect experienced by the user is then kept constant by taking the distance of the user to the lighting device and the pupil size of the user into account and adjusting the spectral composition of the light output, while keeping CCT and lux levels experienced by the user constant.

In an embodiment, the system not only adjust the light output according to the distance between light source and user, but also takes the user's pupil size into account. Whenever the system detects that pupil size has changed, the light output (luminous flux, CCT, and/or spectrum) is modified in order to achieve a constant (with less than 10% change) melanopic illuminance on the retina.

For instance, a mobile device (laptop, smartphone, tablet or smartwatch) may be provided that keeps the melanopic illuminance below 40 melanopic lux in the evening or at night (in order to prevent suppression of the sleep supporting hormone melatonin) when the user brings the device closer to the face.

For instance, in an example a light therapy device is provided, wherein when the user increases the distance to the light therapy device, the system will automatically adjust the melanopic lux levels at the eye to maintain at least 200 melanopic lux at the eye, thus securing effectiveness of the light therapy.

In an embodiment, the control system may adapt the spectral power distribution depending on a light intensity chosen by the user. In embodiments, the control system may apply a 24 dynamic rhythm to one or more lighting properties, such as the melanopic lux value. The invention may be applied in backlights for displays or mobile devices that automatically adjust spectrum depending on the time and an intensity chosen by the user. The invention may be applied in a lighting system that automatically adjusts the CCT and intensity range that a user can choose from depending on the time of day or the current melanopic flux or a desired melanopic flux, or a desired melanopic illuminance.

Figure 2A:
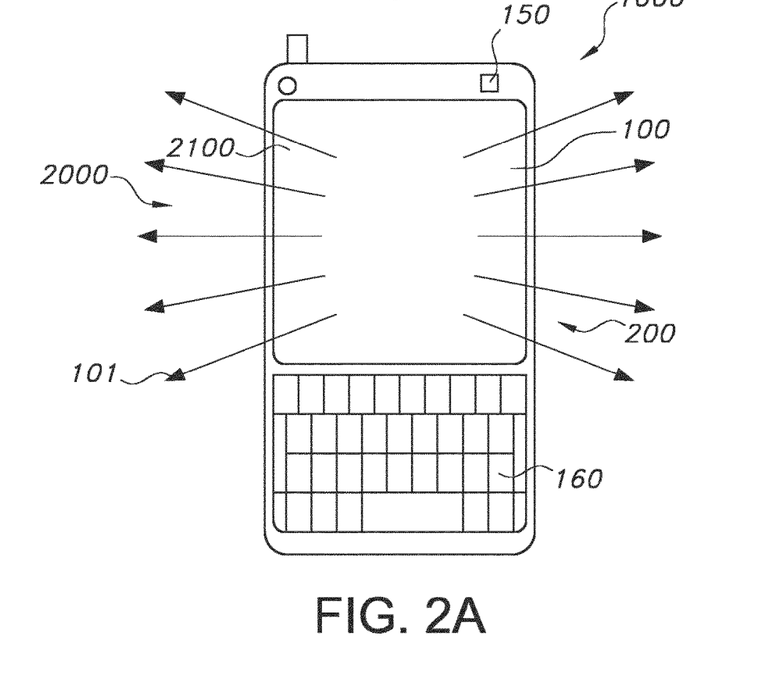
FIGS. 2a-2b schematically depict some aspects of the light emitting system.
Figure 2B:
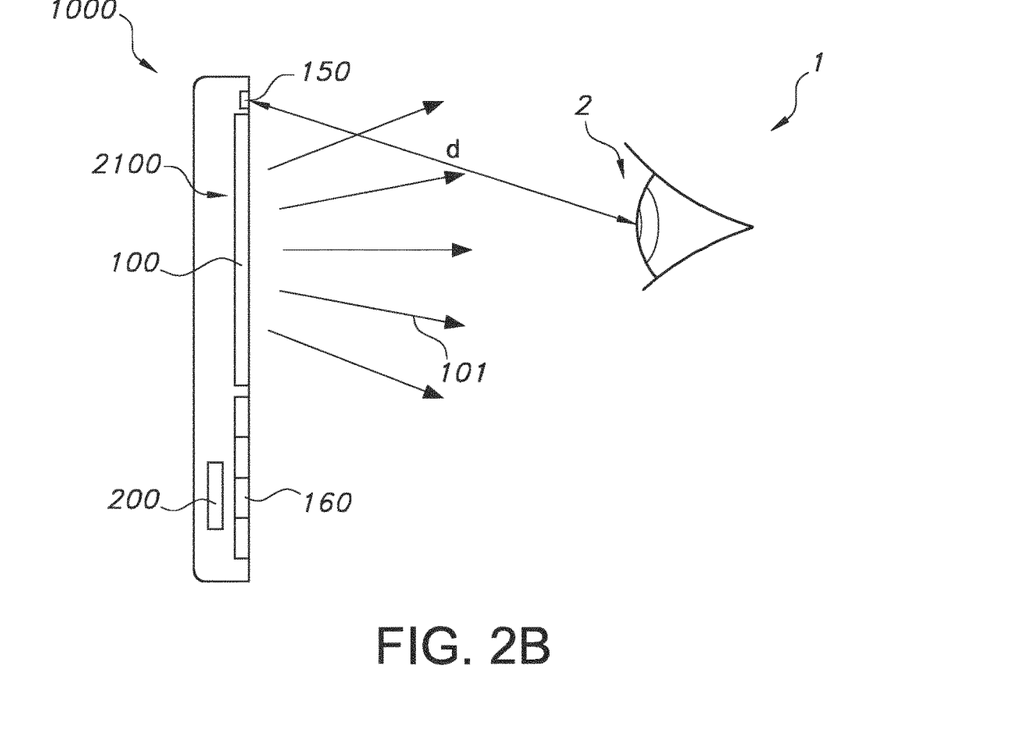

FIGS. 2a-2b schematically depict an embodiment of a light emitting system 1000. The system 1000 comprises a lighting device 100 configured to provide light 101. Further, the system 1000 comprises a sensor 150 configured to sense a user-related parameter selected from one or more of a distance parameter d between the lighting device 100 and a user (very schematically depicted and indicated with reference 1) and an eye-activity parameter of the eye 2 of the user 1. The system also comprises a control system 200. The control system 200 is especially configured to control one or more lighting properties selected from a spectral power distribution of the light 101, and the light intensity I of the light 101 as function of the user-related parameter. FIG. 2*a* by way of example also depicts an embodiments of a portable device 2,000. The portable device 2,000 comprises a display 2100 comprising the lighting device 100. Further, the portable device comprises the sensor 150 and the control system 200. Here, by way of example a cell phone is depicted. Reference 160 indicates a user interface. Of course, the user interface can also be a graphical user interface. The sensor 150 is configured to sense one or more of infrared radiation and reflected light. In this way, the distance parameter can be sensed.

Figure 3A:
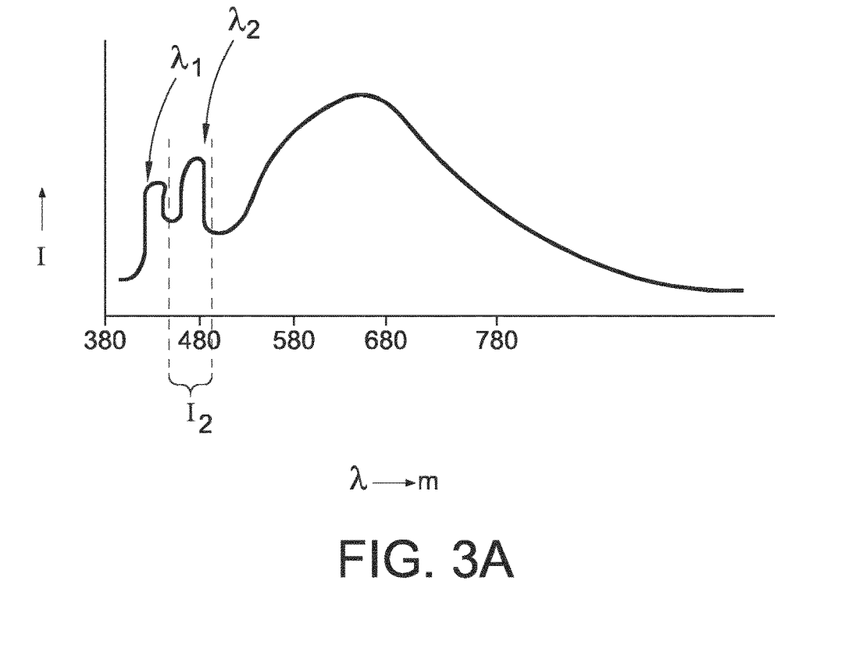
FIGS. 3a-3d schematically show some further aspects of amongst others the system and method as described herein.

FIG. 3*a* schematically depicts a spectral distribution as function of the wavelength. Here, on the y-axis the intensity is indicated in energy values, such as the luminous power in lumen. The references $\lambda_1$ and $\lambda_2$ indicate a short wavelength blue and a long wavelength blue, with a peak maximum in the 400 to 440 nm and the 440 to 490 nm regions respectively. Especially, the maxima may differ at least 20 nm from each other. In one wavelength range the peak may be provided by a first LED and in the other wavelength range the peak may be provided by another LED. Both LEDs may provide blue light. By tuning the relative intensities, the melanopic flux of the combined light output may be changed while still providing blue light. The indication $I_2$ relates to intensity in the spectral range of 440 to 490 nm, which is a range wherein the eye is relative sensitive to circadian rhythm impacting light, see also above. Hence, when the melanopic flux should be reduced, the intensity in this longer wavelength range may be reduced (and in the shorter wavelength range increased); when the melanopic flux should be increased, the intensity in this longer wavelength range may be increased (and in the shorter wavelength range decreased).

Figure 3B:
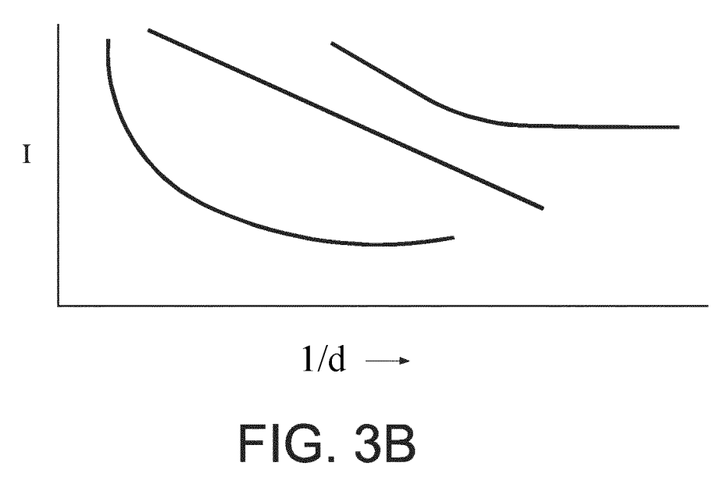

FIG. 3*b* very schematically depicts a number of possible relations that can be implemented by a control system as disclosed herein, between light output, such as intensity (above indicated in an example with $I_1$) or an intensity in the 440 to 490 nm region (above indicated in an example with $I_2$) or melanopic intensity (above indicated in an example with $I_3$), and distance d. The curves from left to right, for instance, the relation can be quadratic, can be partly quadratic and partly linear, can be linear, can be linear until a certain minimum, etc. etc.

Figure 3C:
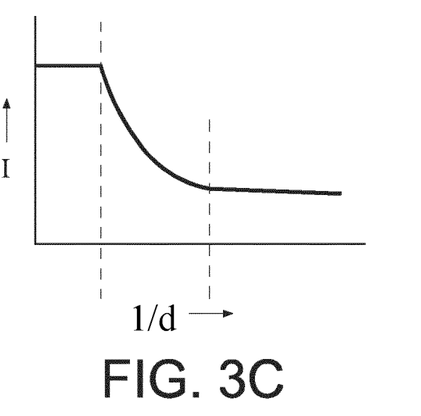

FIG. 3*c* schematically depicts an example of a possible relation that can be implemented by a control system as disclosed herein, between light output, such as an intensity in the 440 to 490 nm region $I_2$ or melanopic intensity $I_3$ and distance d. Both a maximum value (e.g. predetermined by a user) and a minimum value (e.g. predetermined by a user) larger than zero are indicated. In the range between the dashed lines, the system may control the intensity as function of the distance parameter d.

Figure 3D:
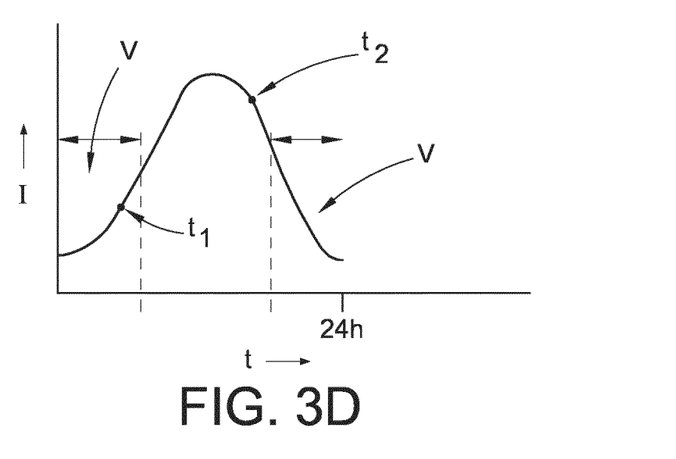

FIG. 3*d* schematically depicts a basic intensity scheme as function of time, such as a predefined daily intensity scheme, wherein e.g. a cell phone display automatically has a low intensity during the night and a larger intensity during the day. In specific regions, indicated with the references V (left from the left dashed line and right from the right dashed line; i.e. the relatively nocturnal times), wherein the intensity may be lower, the intensity may be further modulated according to the invention. Hence, when at t1 the distance between device and user is changed, the intensity may be modulated. However, at t2, a change in distance may not lead to a change in intensity. For instance, during nocturnal times a change in intensity may have impact on the circadian rhythm whereas during the day this may not be the case.

The term "substantially" herein, such as in "substantially all light" or in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. Unless the context clearly requires otherwise, throughout the description and the claims, the words "comprise", "comprising", and the like are to be construed in an inclusive sense as opposed to an exclusive or exhaustive sense, that is to say, in the sense of "including, but not limited to". The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention further applies to a device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

The invention claimed is:

1. A light emitting system comprising:
a lighting device configured to provide light;
a sensor configured to sense a distance parameter d between the lighting device and a user; and
a control system is configured to control one or more lighting properties selected from a spectral power distribution of the light, and a light intensity I of the light as function of the distance parameter d for maintaining the melanopic illuminance at the user constant within a predetermined range of melanopic lux values,
wherein the lighting device is comprised in a portable device, and
wherein the control system is configured to maintain in a mode a value of $I/(\alpha d^n)$ constant over at least part of a range of the distance parameter d, wherein I is the luminous power of the light of the lighting device, and wherein $0<\alpha\leq 1$ and $1\leq n\leq 2$.

2. The light emitting system according to claim 1 wherein the control system is configured to scale the light intensity I of the light with the distance parameter d linearly or exponentially.

3. The light emitting system according claim 1, wherein the control system is configured to maintain in a mode the value of $I/(\alpha d^n)$ constant over at least part of a range of the distance parameter d.

4. The light emitting system according to claim 1, wherein the control system is configured to maintain a predetermined melanopic illuminance, wherein light emitting system further comprises a user interface configured to allow a user determine the predetermined melanopic illuminance.

5. The light emitting system according to claim 1, wherein the control system is configured to control the melanopic illuminance to be not larger than a predetermined maximum melanopic illuminance value and/or to be not smaller than a predetermined minimum melanopic illuminance value.

6. The light emitting system according to claim 1, wherein the control system is configured to control the one or more lighting properties selected from the spectral power distribution of the light, and the light intensity of the light as function of the distance parameter d, while maintaining one or more other lighting properties constant, wherein the one or more other light properties are selected from the group consisting of the correlated color temperature and the color point.

7. The light emitting system according to claim 1, wherein the control system is configured to adapt the one or more lighting properties selected from a spectral power distribution of the light, and the light intensity of the light as function of a change in the distance parameter d, wherein the adaptation is only executed after a predetermined period when the change is permanent within the predetermined period.

8. The light emitting system according to claim 1, wherein the control system is configured to one or more of adapting the one or more lighting properties selected from a spectral power distribution of the light and the light intensity I of the light as function of an average change in the user-related parameter, and gradually adapting the one or more lighting properties as function of a change in the distance parameter d.

9. The light emitting system according to claim 1, wherein the control system is configured to control the light according to a predefined scheme, and wherein the control system is further configured to adapt the light relative to the predefined scheme as function of the distance parameter d.

10. The light emitting system according to claim 1, comprising a portable device, wherein the portable device comprises a display comprising the lighting device, wherein the portable device further comprises the sensor and the control system, wherein the portable device is selected from the group consisting of a smartphone, a laptop, a tablet, a wearable device, a personal digital assistant, a game console, a media player, and a navigation device; and wherein the sensor is configured to sense one or more of infrared radiation and reflected light.

11. The light emitting system according to claim 1, wherein the lighting device comprises a source of deep blue light, a source of blue light, a source of green light, and a source of red light, which are independently controllable by the control system, wherein the source of deep blue light is configured to generate light selected from the wavelength range of 400-440 nm, and wherein the light of the source of deep blue light has a peak maximum having a smaller wavelength then a peak maximum of the light of the source of blue light.

12. A method of controlling light, wherein one or more lighting properties, including the spectral power distribution and the intensity of the light are controllable, the method comprising: providing light from a portable lighting device; sensing a distance parameter d between the lighting device and a user; and controlling one or more lighting properties selected from a spectral power distribution of the light and a light intensity of the light as function of the distance parameter d for maintaining the melanopic illuminance at the user constant within a predetermined range of the melanopic lux values, and maintaining in a mode a value of $I/(\alpha d^n)$ constant over at least part of a range of the distance parameter d, wherein I is the luminous power of the light of the lighting device, and wherein $0<\alpha\leq 1$ and $1\leq n\leq 2$.

13. A computer program product, when running on a computer which is functionally coupled to a portable lighting device, is capable of bringing about the method as described in claim 12, wherein the lighting device is configured to provide light, wherein one or more lighting properties, including the spectral power distribution and the intensity of the light, are controllable.

14. A light emitting system comprising:
a lighting device configured to provide light;
a sensor configured to sense a distance parameter d between the lighting device and a user; and
a control system is configured to control one or more lighting properties selected from a spectral power distribution of the light, and a light intensity I of the light as function of the distance parameter d for maintaining the melanopic illuminance at the user constant within a predetermined range of melanopic lux values,
wherein the lighting device is comprised in a portable device, and
wherein the light emitting system is configured to maintain a value of $\Phi_{mel}/(\alpha d^n)$ constant over at least part of a range of the distance parameter d, wherein $\Phi_{mel}$ is the melanopic flux of the light of the lighting device, and wherein $0<\alpha\leq 1$ and $1\leq n\leq 2$.

15. The light emitting system according claim 14, wherein the control system is configured to maintain the value of value of $\Phi_{mel}/(\alpha d'')$ constant over at least another part of a range of the distance parameter d.

16. The light emitting system according to claim 14, wherein the control system is configured to control the one or more lighting properties selected from the spectral power distribution of the light, and the light intensity of the light as function of the distance parameter d, while maintaining one or more other lighting properties constant, wherein the one or more other light properties are selected from the group consisting of the correlated color temperature and the color point.

17. The light emitting system according to claim 14, wherein the control system is configured to adapt the one or more lighting properties selected from a spectral power distribution of the light, and the light intensity of the light as function of a change in the distance parameter d, wherein the adaptation is only executed after a predetermined period when the change is permanent within the predetermined period.

18. The light emitting system according to claim 14, wherein the control system is configured to one or more of adapting the one or more lighting properties selected from a spectral power distribution of the light and the light intensity I of the light as function of an average change in the user-related parameter, and gradually adapting the one or more lighting properties as function of a change in the distance parameter d.

\* \* \* \* \*